United States Patent [19]

Reicheneder et al.

[11] 3,975,526

[45] Aug. 17, 1976

[54] SYMPATHICOMIMETIC REMEDY INDUCING VASOPRESSOR EFFECTS AFTER ORAL AND PARENTERAL ADMINISTRATION

[75] Inventors: Franz Reicheneder, Ludwigshafen; Rudolf Kropp, Limburgerhof; August Amann, Ludwigshafen; Hubert Giertz, Limburgerhof; Joerg Schuster, Viernheim, all of Germany

[73] Assignee: Badische Anilin- & Soda-Fabrik Aktiengesellschaft, Ludwigshafen (Rhine), Germany

[22] Filed: June 10, 1974

[21] Appl. No.: 478,107

Related U.S. Application Data

[63] Continuation of Ser. No. 276,935, Aug. 1, 1972, abandoned.

[30] Foreign Application Priority Data

Aug. 7, 1971  Germany............................ 2139687

[52] U.S. Cl. ............................................... 424/250
[51] Int. Cl.² ....................................... A61K 31/495
[58] Field of Search .................................... 424/250

[56] References Cited

UNITED STATES PATENTS

| 2,891,953 | 6/1959 | Clark | 260/250 A |
| 3,631,038 | 12/1971 | Reicheneder et al. | 260/247.5 |

Primary Examiner—Jerome D. Goldberg
Assistant Examiner—Daren M. Stephens
Attorney, Agent, or Firm—Johnston, Keil, Thompson & Shurtleff

[57] ABSTRACT

Cardiac stimulants and vasopressor agents for peroral and parenteral administration containing 6-alkoxy-pyridazinium compounds as active ingredients.

12 Claims, No Drawings

SYMPATHICOMIMETIC REMEDY INDUCING VASOPRESSOR EFFECTS AFTER ORAL AND PARENTERAL ADMINISTRATION

This is a continuation of application Ser. No. 276,935, filed 8-1-72 and now abandoned.

Many chemical compounds are known which are effective as vasopressor agents when administered perorally. However, resorption of these compounds from the intestines is generally only poor, with the result that their action is not reliable and usually of only short duration. There is thus a need for agents which afford good resorption from the gastrointestinal tract combined with a long period of activity and a broad therapeutic effect and which may also be effectively administered parenterally if desired.

We have now found that compounds having a cation of the following formula:

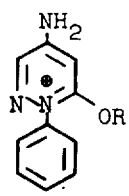

wherein R is alkyl of from 1 to 4 carbon atoms, produce remarkable cardiac stimulating effects and cause prolonged vasopressor activity in man but have less detrimental side-effects compared with e.g. ergotamine. In general, the prolonged period of activity and the good range of therapeutical applications of the agents containing said compounds as active ingredients should be stressed in the case of peroral or parenteral administration.

The compounds have a sympathomimetic effect which is accompanied by a sympatholytic component when very high doses are administered. They are capable of much better resorption from the gastrointestinal tract than known agents. The ratio of the perorally effective dosage to the intravenously effective dosage is, according to our own tests, very much smaller than in the case of, say, ethyl norphenylephrine or Norfenefrin. Poor resorbtion is also found with other vasopressor sympathomimetic agents, for example oxedrine (cf. Kurzes Lehrbuch der Pharmakologie by Kuschinsky and Lullmann).

The therapeutic index (ratio of the lethal dosage to minimum effective dosage) of the compound in which R is methyl is excellent in dogs, rabbits, cats, rats and mice. Its value is lowest in the dog, where it is about 75. Dogs will tolerate doses of 25 mg/kg/day for 90 days without substantial damage. In the dog and cat, the threshold dose is less than 0.1 mg/kg for intravenous administration and 1 mg/kg for peroral administration.

In man, the therapeutic dosage is from about 10 to 70 mg when administered perorally in separate doses of generally about 20 mg two to three times a day. A single larger dose of, say, 70 mg may be tolerated without side-effects. The antihypotonic effect may also be accompanied by good activity against migraine. Parenteral doses are in the range of from approx. 1 to 10 mg.

The compounds may also be administered in combination with other active ingredients, for example caffeine or analgesic agents.

Suitable pharmaceutical compositions containing the above active ingredients are the conventional preparations for oral administration, namely tablets, dragees, powders and drops. Parenteral administration is effected using injectable solutions containing the active ingredient and prepared in conventional manner.

The compounds which are stable and water-soluble may be obtained by reaction of pyridazones of the formula

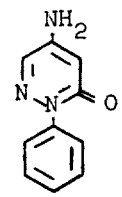

with the appropriate alkyl sulfates, aryl sulfonates and triethyloxonium tetrafluoroborate. Further details may be found in U.S. Pat. Spec. No. 3,631,038. The introduction of anions into these compounds may be effected by the use of acids providing ions which are therapeutically acceptable in normal doses, for example the anions of hydrochloric acid, hydrobromic acid, hydriodic acid, perchloric acid, fluoroboric acid, sulfuric acid, phosphoric acid and nitric acid. Instead of inorganic acids, organic acids such as aliphatic mono-, di- or tricarboxylic acids may be used. Examples of such acids are formic acid, acetic acid, trifluoroacetic acid, propionic acid, glycollic acid, lactic acid, tartaric acid, pyruvic acid, citric acid, oxalic acid, malinic acid, succinic acid, maleic acid, benzoic acid and amino acids such as lysine, arginine and glutaric acid. Other examples are aromatic acids, benzoic acid, salicylic acid, aminobenzoic acid and also heterocyclic acids such as nicotinic acid. The man skilled in the art will known the pharmaceutically acceptable anions cationic the catinic active ingredients from the literature.

Of particular interest is the compound in which R is $CH_3$ as follows

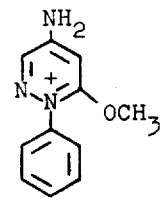

and in which the anion is chloride, ethosulfate, tosylate or, preferably, methosulfate. When R is $CH_3$, the melting point of the methosulfate is 173°–174°C, that of the perchlorate being 179°–182°C and that of the tosylate being 169°–171°C. The other homologs (in which R is ethyl, propyl, isopropyl, butyl, isobutyl or t-butyl) also provide pharmaceuticals having the above remarkable properties.

The following examples of pharmaceutical compositions do not indicate limitations of the amount of active ingredient present in the final formulations but are simply intended to illustrate some of the possible forms of composition.

EXAMPLE 1

| Composition of a tablet: | mg |
|---|---|
| active ingredient | 20.0 |
| lactose | 41.5 |
| microcrystalline cellulose | 16.0 |
| magnesium stearate | 2.5 |
| | 80.0 |

The components are mixed by conventional galenic methods and compressed to tablets by the usual means.
Injectable compositions

EXAMPLE 2

| active ingredient | 100.0 mg |
|---|---|
| sodium chloride | 17,900.0 mg |
| injection water to | 2,000.0 ml | so as to give a solution containing 0.05 mg/l of active ingredient. The solution is filtered sterile through a membrane filter of 0.2μ (Sartorius 1,307) and is filled into 1 ml ampoules under a blanket of nitrogen. The ampoules are sterilized in steam at 120°C for 20 minutes.

EXAMPLE 3

Example 2 is repeated using the following components, but without the use of a blanket of nitrogen:

| active ingredient | 50.0 mg |
|---|---|
| sodium chloride | 4,450.0 mg |
| injection water to | 500.0 ml |

The solution contains 0.1 mg/l of active ingredient.

EXAMPLE 4

Example 3 is repeated using the following components to give a solution containing 0.5 mg/l of active ingredient:

| active ingredient | 500.0 mg |
|---|---|
| sodium chloride | 8,500.0 mg |
| injection water to | 100.0 ml |

EXAMPLE 5

Example 2 is repeated using the following components to give a solution containing 2.5 mg/l of active ingredient:

| active ingredient | 2,500.0 mg |
|---|---|
| sodium chloride | 6,500.0 mg |
| injection water to | 100.0 ml |

In these Examples, the active ingredient used is the methosulfate of the compound in which R is CH₃. Alternatively, use may be made of, say, the chloride or perchlorate or any of the other alkyl homologs.

We claim:

1. A composition in dosage form for cardiac stimulation or for increasing blood pressure comprising (1) a carrier and (2) as the active ingredient a pharmaceutically effective amount of a compound having the formula:

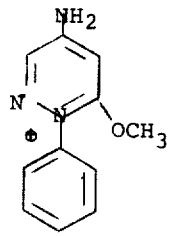

wherein R is alkyl of from 1 to 4 carbon atoms and A⁻ is a pharmaceutically acceptable anion, the amount of said active ingredient in each dose being from about 1 to 70 mg.

2. A composition as set forth in claim 1 containing as the active ingredient a compound of the formula:

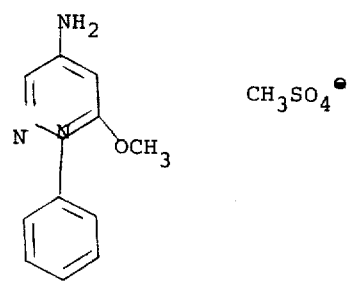

wherein A⁻ is an anion selected from the group consisting of chloride, ethosulfate, tosylate and methosulfate.

3. A composition as set forth in claim 1 containing as the active ingredient a compound of the formula:

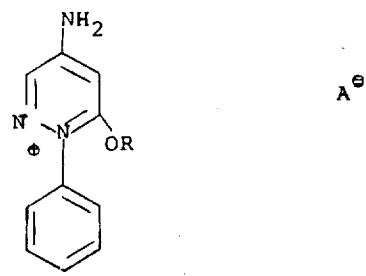

4. A composition in dosage form for cardiac stimulation or for increasing blood pressure comprising (1) a carrier and (2) as the active ingredient a pharmaceutically effective amount of a compound having the formula:

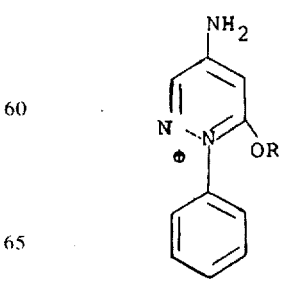

5. A composition in dosage form for cardiac stimulation or for increasing blood pressure comprising (1) a carrier and (2) as the active ingredient a pharmaceutically effective amount of a compound having the formula:

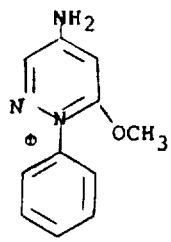

wherein R is alkyl of from 1 to 4 carbon atoms and A⁻ is a pharmaceutically acceptable anion, said composition being in the form of an injectable solution containing from about 1 to 10 mg per dosage of said active ingredient.

6. A composition in dosage form as set forth in claim 4 wherein said active ingredient is a compound of the formula:

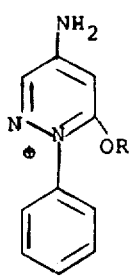

7. A method for cardiac stimulation or to increase the blood pressure in an animal which comprises: administering to said animal in need thereof in dosage form an effective cardiac stimulating or blood pressure increasing amount of a composition comprising (1) a carrier and (2) as the active ingredient a compound having the formula:

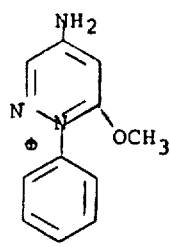

wherein R is alkyl of from 1 to 4 carbon atoms and A⁻ is a pharmaceutically acceptable anion.

8. A method as set forth in claim 7 wherein said active ingredient is a compound of the formula

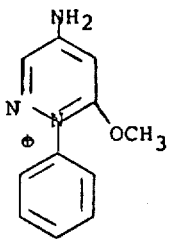

wherein A⁻ is an anion selected from the group consisting of chloride, ethosulfate, tosylate and methosulfate.

9. A method as set forth in claim 7 wherein said active ingredient is a compound of the formula:

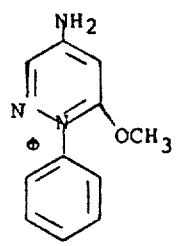

10. A method as set forth in claim 7 wherein said composition is administered parenterally in a dosage of from 1 to 10 mg of said active ingredient.

11. A method as set forth in claim 7 wherein said composition is administered perorally in a dosage of from 10 to 70 mg of said active ingredient.

12. A method as set forth in claim 9 wherein said active ingredient is administered parenterally in a dosage of from 1 to 10 mg of said active ingredient.

* * * * *